(12) United States Patent
Quinn et al.

(10) Patent No.: US 7,585,509 B2
(45) Date of Patent: Sep. 8, 2009

(54) ERB-2 RECEPTOR TARGETING PEPTIDE

(75) Inventors: Thomas P. Quinn, Columbia, MO (US); Natalia G. Karasseva, Columbia, MO (US)

(73) Assignee: The Curators of The University of Missouri, Columbia, MO (US)

( * ) Notice: Subject to any disclaimer, the term of this patent is extended or adjusted under 35 U.S.C. 154(b) by 249 days.

(21) Appl. No.: 10/520,408

(22) PCT Filed: Jul. 3, 2003

(86) PCT No.: PCT/US03/21150

§ 371 (c)(1), (2), (4) Date: May 17, 2005

(87) PCT Pub. No.: WO2004/005320

PCT Pub. Date: Jan. 15, 2004

(65) Prior Publication Data

US 2005/0220706 A1     Oct. 6, 2005

Related U.S. Application Data

(60) Provisional application No. 60/394,174, filed on Jul. 3, 2002.

(51) Int. Cl.
*A61K 39/395* (2006.01)
*A61K 51/08* (2006.01)
*C07K 19/00* (2006.01)
*C07K 7/06* (2006.01)
*A61K 38/08* (2006.01)

(52) U.S. Cl. .............. 424/195.11; 424/184.1; 424/185.1; 424/192.1; 424/193.1; 424/1.11; 424/1.53; 424/1.57; 424/1.69; 514/2; 514/16; 530/329; 530/350; 530/402

(58) Field of Classification Search ................ 424/1.11, 424/1.53, 1.57, 1.69, 9.1, 9.34, 1.81, 9.13, 424/9.322, 193.1, 194.1, 1.65, 195.11, 184.1, 424/185.1, 192.1; 514/2, 16, 44; 530/402, 530/329, 350

See application file for complete search history.

(56) References Cited

U.S. PATENT DOCUMENTS

| | | | | |
|---|---|---|---|---|
| 5,578,482 A | 11/1996 | Lippman et al. | ............ | 435/384 |
| 5,874,528 A | 2/1999 | Lupu et al. | ................. | 530/317 |
| 5,985,553 A | 11/1999 | King et al. | ................. | 435/6 |
| 6,414,130 B1 | 7/2002 | Doherty et al. | ............ | 536/23.5 |
| 6,417,168 B1 | 7/2002 | Greene et al. | ................. | 514/44 |
| 6,426,400 B1 | 7/2002 | Zalutsky | ................... | 530/330 |
| 6,884,418 B1 | 4/2005 | Shawver et al. | .......... | 424/155.1 |

OTHER PUBLICATIONS

Karasseva, N.G. et al., Journal of Protein Chemistry, 21(4): 287-296, May 2002.*
Thakur, M.L. et al., J. Nuclear Medicine, 41: 107-110, 2000.*
Langer, M. et al. Curr. Med. Chem., Anti-Cancer Agents, 1: 71-93, 2001.*
Shoji, Y. and Nakashima, H., Current Pharmaceutical Design, 10: 785-796, 2004.*
Opalinska, J. and Gewirtz, A.M., Nature Reviews, 1: 503-514, 2002).*
Braasch, D.A. and Corey, D.R., Biochemistry, 41(14): 4503-4510, 2002.*
Verma, Nature, 1997, vol. 389, pp. 239-242.*
Favoro, E., et al., Current Opinion Mol. Ther., 9(5): 477-482, 2007; abstract only.*
Rubyani, G.M., Molecular Aspects of Medicine, 22: 113-142, 2001.*
McInnes and Sykes, "Growth Factor Receptors: Structure, Mechanism, and Drug Discovery", *Biopolymers*, 43(5):339-366, 1997.
Oldenburg et al., "Peptide ligands for a sugar-binding protein isolated from a random peptide library", *Proc. Natl. Acad. Sci., USA*, 89:5393-5397, 1992.
Piccart, Perry (Ed.), American Soc. Clinical Oncology, Alexandria, VA, Integration of New Therapies Into Management of Metastatic Breast Cancer: A Focus on Chemotherapy, Treatment Selection Through Use of Molecular Markers, and Newly Developed Biologic Therapies in Late Clinical Development. "In: *American Society of Clinical Oncology Educational Book*", 1999.
Weiner et al., "Phase I Trial of 2B1, a Bispecific Monoclonal Antibody Targeting c-erbB-2 and FeγRIII" *Cancer Res.*, 55(20):4586-4593, 1995.
Wiechen et al., "C-erbB-2 anti-sense phosphorothioate oligodeoxynucleotides inhibit growth and serum-induced cell spreading of p185$^{c\text{-}erbb\text{-}2}$ overexpressing ovarian carcinoma cells" *Int. J. Cancer* 63(4):604-608, 1995.
Wrighton et al., "Small Peptides as Potent Mimetics of the Protein Hormone Erythropoietin" *Science* 273, 458-463, 1996.
Alimandi et al. "Epidermal growth factor and betacellulin mediate signal transduction through co-expressed ErbB2 and ErbB3 receptors", *EMBO J*, 16(18):5608-5617, 1997.
Ballinger et al., "Selection of Heregulin Variants Having Higher Affinity for the ErbB3 Receptor by Monovalent Phage Display", *J Biol. Chem.*, 273(19): 11675-11684, 1998.
Baselga et al., "Recombinant Humanized Anti-HER2 Antibody (Herceptin™) Enhances the Antitumor Activity of Paclitaxel and Doxorubicin against HER2/*neu* Overexpressing Human Breast Cancer Xenografts", *Cancer Res.*,58:2825-2831, 1998.
Devlin et al., "Random Peptide Libraries: A Source of Specific Protein Binding Molecules", *Science*, 249:404-406, 1990.

(Continued)

*Primary Examiner*—Alana M. Harris
*Assistant Examiner*—Anne L Holleran
(74) *Attorney, Agent, or Firm*—Fulbright & Jaworski, LLP

(57) ABSTRACT

The ErbB-2 receptor, a member of the tyrosine kinase type 1 family of receptors, has been implicated in many human malignancies. Bacteriophage display technology was employed to identify peptides that bound to the extracellular domain of human ErbB-2. The peptide KCCYSL, most frequently occurring in the affinity selected population, was chemically synthesized and characterized for its binding activities to the recombinant extracellular domain of ErbB-2. The synthetic peptide exhibits high specificity to ErbB-2 as well as to ErbB-1, another member of ErbB family. Thus, this peptide can be employed in cancer imaging or therapeutic agent targeting to malignant cells ErbB-2 receptor.

21 Claims, 3 Drawing Sheets

OTHER PUBLICATIONS

Disis et al., "Generation of Immunity to the Her-2/neu Oncogenic Protein in Patients with Breast and Ovarian Cancer Using a Peptide-based Vaccine", *Clin. Cancer Res.*, 5(6):1289-1297, 1999.

Giebel et al., "Screening of Cyclic Peptide Phage Libraries Identifies Ligands That Bind Streptavidin with High Affinities" *Biochemistry*, 34:15430-15435, 1995.

Jones et al., "Binding Interaction of the Heregulinβ egf Domain with ErbB3 and ErbB4 Receptors Assessed by Alanine Scanning Mutagenesis", *J. Biol. Chem.*, 273(9):11667-11674, 1998.

Kay et al., "An M13 phage library displaying random 38-amino-acid peptides as a source of novel sequences with affinity to selected targets", *Gene* 128:59-65, 1993.

Harris et al., "Gene therapy for cancer using tumour-specific prod", *Gene Therapy*, 1:170-5, (1994).

Jinno et al., "Effectiveness of an Adriamycin Immunoconjugate that Recognizes the C-*erb*B-2 Product on Breast Cancer Cell Lines", *Surgery today*, 26:501-7, (1996).

\* cited by examiner

FIG. 2A
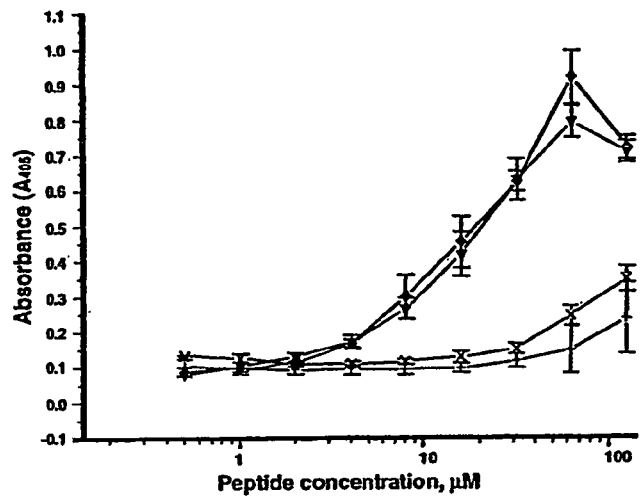
FIG. 2B
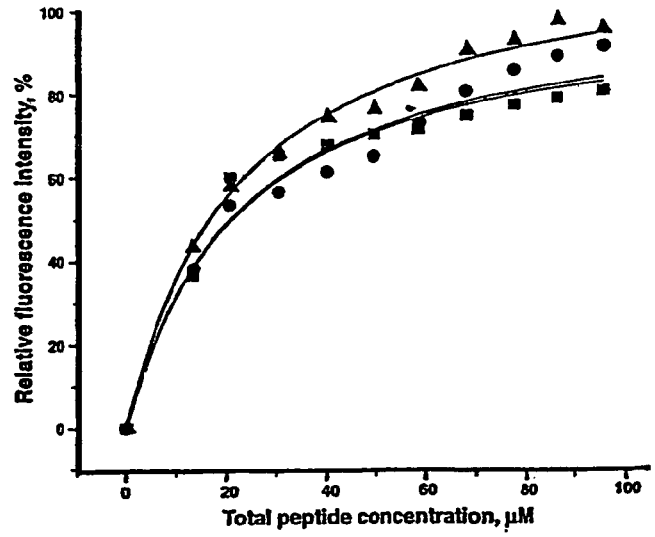
FIG. 2C

FIG. 3A
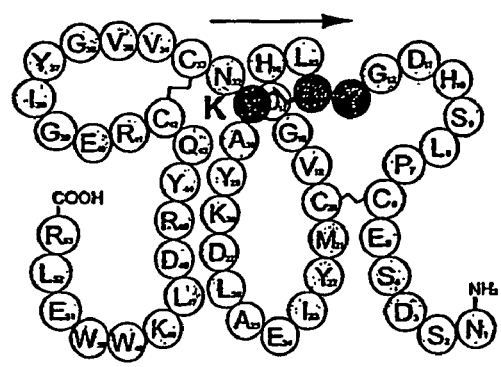
FIG. 3B
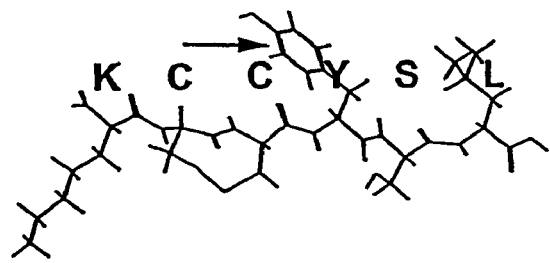
FIG. 3C
```
EGF     YCLHDGVCMYIEALD----KYACN
TGF-α   FCFH-GTCRFLVQED----KPACV
AR      FCIH-GECKYIEHLE----AVTCK
HB-EGF  FCIH-GECKYVKELR----APSCI
BC      YCIH-GRCRFVVDEQ----TPSCI
HRG-α   FCVNGGECFMVKDLSNPSRYLCK
HRG-β   FCVNGGECFMVKDLSNPSRYLCK
```

ERB-2 RECEPTOR TARGETING PEPTIDE

This application claims priority to PCT/us2003/021150, filed on Jul. 3, 2003, which claims priority to U.S. Provisional Application No. 60/394,174 filed Jul. 3, 2002, the entire contents of which are hereby incorporated by reference.

The government has rights in the present invention pursuant to funding from the Department of the Army, Grant No. DAMD17-00-0351 and Grant No. DAMD17-97-1-7198.

BACKGROUND OF THE INVENTION

The present invention claims priority to application U.S. Provisional Patent Application Serial No. 60/394,174 filed on Jul. 3, 2002. The entire text of the above-referenced disclosure is specifically incorporated herein by reference without disclaimer.

A. Field of the Invention

The invention pertains to the fields of oncology, protein structure and function, and molecular biology. More particularly, the invention relates to the identification of ErbB-2 binding peptides and their use in cancer diagnosis and therapy.

B. Related Art

The erbB-2 proto-oncogene, also known as HER-2 or neu, is frequently altered in human cancers (Hynes and Stem, 1994). ErbB-2, along with three other known homologous proteins, ErbB-1 (epidermal growth factor receptor, EGFR), ErbB-3, and ErbB-4, form the ErbB family or subclass I of receptor tyrosine kinases (RTK)(McInnes and Sykes, 1997). The activation of ErbB receptors leads to stimulation of cell growth and division. Signal transduction in this class of receptor proteins is initiated through the binding of a growth factor to the extracellular domain of the receptor, followed by receptor homo- or heterodimerization, activation of intracellular kinase domain, and tyrosine autophosphorylation (McInnes and Sykes, 1997).

The ligands for the ErbB growth factor receptor tyrosine kinase family are numerous yet similar. All of them are structurally homologous and contain an epidermal growth factor (EGF)-like motif with six cysteines at highly conserved positions defining three disulfide loops that give rise to the tricyclic nature of these proteins. Despite their receptor specificity, most of the ErbB ligands are capable of binding several different receptors. EGF, transforming growth factor α, and betacellulin bind ErbB1 and the ErbB2/ErbB3 heterodimer (Alimandi et al., 1997); neuregulins associate with ErbB-3 and ErbB-4 (Jones et al., 1998); and epiregulin was shown to complex all three receptors, i.e. ErbB-1, ErbB-3, and ErbB-4 (Shelly et al., 1998). No ligand has been found that binds directly to ErbB-2.

Gene amplification and overexpression of ErbB-2 is associated with increased rates of tumor growth and enhanced rates of metastases (Hynes and Stem, 1994). Although ErbB-2 is also expressed at low levels in several normal organs and tissues (De Potter et al., 1989), the elevated levels of ErbB-2 in many human malignancies and its extracellular accessibility makes it an attractive target for the development of tumor-specific agents. The ErbB-2 receptor has been targeted by a variety of substances and modalities, including monoclonal antibodies (Weiner et al., 1995), immunoconjugates (Jinno et al. 1996), vaccines (Disis et al., 1999), antisense therapy (Wiechen et al., 1995) and gene therapy (Harris et al., 1994). Recently Herceptin™, a humanized monoclonal antibody against ErbB-2 (Baselga et al., 1998), was approved for the treatment of metastatic breast cancer. Herceptin™ was shown to possess the anti-tumor activity, but it was also found to aggravate doxorubicin-induced cardiac dysfunction and, possibly, be cardiotoxic on its own (Piccart, 1999). Thus, there remains a need to identify improved ErbB-2-specific reagents for the treatment of ErbB-2 related cancers.

SUMMARY OF THE INVENTION

Thus, in accordance with the present invention, there are provided methods for targeting an agent to a cell expressing ErbB-2 comprising bringing the cancer cell into contact with a peptide-agent complex, wherein the peptide comprises the sequence KCCYSL (SEQ ID NO:1). The agent may be a diagnostic agent, such as a radiolabel, a chemilluminescent label, a fluorescent label, a magnetic spin resonance label, or a dye. Radiolabels include astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, lutetium$^{177}$, samarium$^{153}$, holmium$^{166}$, bisumth$^{212}$, bisumuth$^{213}$ and actinium$^{225}$. Alternatively, the agent may be a therapeutic agent, such as a chemotherapeutic agent, a radiotherapeutic agent, a toxin, a cytokine or a nucleic acid construct.

Generally, the peptide will be between 6 and about 100 residues in length, more particularly between 6 and about 50 residues in length, more particularly between 6 and about 25 residues in length, and more particularly between about 6 and 15 residues in length. The cell may be a cancer cell, such as a breast cancer cell or a prostate cancer cell. The complex may further comprise a linking moiety that connects the agent and the peptide, wherein the linking moiety may be linked to the peptide through the N-terminal amine, the C-terminal carboxyl group, or a side chain. The cell may be located in a subject, such as a human. The complex may thus be delivered locally or regionally to the cell; the complex may be delivered systemically as well. The complex may also be delivered into vasculature of a tumor comprising the cell.

In another embodiment, there are provided methods for diagnosing ErbB-2-positive cancer in a subject comprising (a) administering to the subject a peptide-diagnostic agent complex, wherein the peptide comprises the sequence KCCYSL; and (b) assessing the amount and/or localization in the subject, of the diagnostic agent. The diagnostic agent may be a radiolabel, a chemilluminescent label, a fluorescent label, a magnetic spin resonance label, or a dye. Radiolabels include astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, lutetium$^{177}$, samarium$^{153}$, holmium$^{166}$, bisumth$^{212}$, bisumuth$^{213}$ and actinium$^{225}$.

Generally, the peptide will be between 6 and about 100 residues in length, more particularly between 6 and about 50 residues in length, more particularly between 6 and about 25 residues in length, and more particularly between about 6 and 15 residues in length. The subject may suffer from breast cancer or a prostate cancer. The complex may further comprise a linking moiety that connects the agent and the peptide, wherein the linking moiety may be linked to the peptide through the N-terminal amine, the C-terminal carboxyl group, or a side chain. The complex may thus be delivered locally or regionally to the tumor; the complex may be delivered systemically as well. The complex may also be delivered into vasculature of the tumor.

The patient may or may not have been previously diagnosed with cancer. The patient may has previously received a cancer therapy, or may be concurrently receiving a cancer therapy. The may be patient at an elevated risk for cancer. The assessing may comprise organ or whole body imaging, and may further comprise excising a tumor localized by the diagnostic agent.

In yet another embodiment, there are provided methods for treating an ErbB-2-positive cancer in a subject in need thereof comprising administering to the subject a peptide-therapeutic agent complex, wherein the peptide comprises the sequence KCCYSL. The therapeutic agent may be a chemotherapeutic agent, a radiotherapeutic agent, a toxin, a cytokine or a nucleic acid construct. The radiolabel may be astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, lutetium$^{177}$, samarium$^{153}$, holmium$^{166}$, bisumth$^{212}$, bisumuth$^{213}$ and actinium$^{225}$.

Generally, the peptide will be between 6 and about 100 residues in length, more particularly between 6 and about 50 residues in length, more particularly between 6 and about 25 residues in length, and more particularly between about 6 and 15 residues in length. The complex may further comprise a linking moiety that connects the agent and the peptide, wherein the linking moiety may be linked to the peptide through the N-terminal amine, the C-terminal carboxyl group, or a side chain. The cancer may be breast cancer or prostate cancer. The complex may be administered more than once, may be delivered local or regional to a tumor, or may be delivered systemically. The method may further comprise administering a second distinct cancer therapy, such as radiotherapy, chemotherapy, immunotherapy or surgery.

Also included are methods for rendering an unresectable ErbB-2-positive tumor resectable comprising administering to a subject having the tumor a peptide-therapeutic agent complex, wherein the peptide comprises the sequence KCCYSL; methods for treating metastatic ErbB-2-positive cancer comprising administering to a subject in need thereof a peptide-therapeutic agent complex, wherein the peptide comprises the sequence KCCYSL; methods for preventing recurrent ErbB-2-positive cancer comprising administering to a subject having been successfully treated for ErbB-2-positive cancer a peptide-therapeutic agent complex, wherein the peptide comprises the sequence KCCYSL; and methods for treating microscopic residual disease in ErbB-2-positive cancer comprising administering to a subject, following tumor resection, a peptide-therapeutic agent complex, wherein the peptide comprises the sequence KCCYSL.

In still yet another embodiment, there is provided a peptide-agent complex, wherein the peptide comprises the sequence KCCYSL. The agent may be a diagnostic agent, as set forth above, or a therapeutic agent, also as set forth above. Generally, the peptide will be between 6 and about 100 residues in length, more particularly between 6 and about 50 residues in length, more particularly between 6 and about 25 residues in length, and more particularly between about 6 and 15 residues in length. The complex may further comprise a linking moiety that connects the agent and the peptide, wherein the linking moiety may be linked to the peptide through the N-terminal amine, the C-terminal carboxyl group, or a side chain.

In still yet a further embodiment, there is provided a pharmaceutical composition comprising a peptide-agent complex, wherein the peptide comprises the sequence KCCYSL. The agent may be a diagnostic agent, as set forth above, or a therapeutic agent, also as set forth above. Generally, the peptide will be between 6 and about 100 residues in length, more particularly between 6 and about 50 residues in length, more particularly between 6 and about 25 residues in length, and more particularly between about 6 and 15 residues in length. The complex may further comprise a linking moiety that connects the agent and the peptide, wherein the linking moiety may be linked to the peptide through the N-terminal amine, the C-terminal carboxyl group, or a side chain.

Also provided are kits comprising peptide-agent complex in a suitable container, wherein the peptide comprises the sequence KCCYSL. Also provided are isolated and purified peptide compositions comprising a peptide comprising the sequence KCCYSL and a linker molecule coupled to the peptide, wherein the linker comprises a free reactive group.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2C—Immunoblot analysis of the binding activity of biotinylated synthetic p6.1 peptide (100 pM) to the recombinant human ErbB-2-ECD, bovine serum albumin (BSA), bovine asialofetuin (ASF), and human IgG (FIG. 2B). The quantities of immobilized proteins (in ng) are given on the top. FIG. 2B—Binding profiles of biotinylated p6.1 and biotinylated control peptide (CP) to immobilized recombinant ErbB-2-ECD (▼-▼ p6.1, +-+ CP), and ErbB-1 (♦-♦ p6.1, x-x CP). FIG. 2C—Fluorescent titration of the ErbB-2-ECD with synthetic p6.1 peptide at 0.2 μM protein (■), 0.4 μM protein (●), and 0.6 μM protein (▲).

FIG. 3A-3C—Schematic presentation of the EGF primary structure arranged to demonstrate the formation of CCY motif due to $C_{14}$-$C_{31}$ disulfide bond (FIG. 3A). The letter K next to $N_{32}$ indicates the lysine corresponding to $K_{71}$ of AR, and $K_{11}$ of HRG-α and HRG-β. FIG. 3B—Backbone structure of oxidized form of p6.1 peptide. FIG. 3C—Sequence alignment of the amino acids 13-32 fragment of EGF with corresponding fragments of several other ErbB ligands. The amino acid residues participating in formation of KCCY/F motif colored in red. Arrows, indicate a direction of the KCCY/F motif.

DETAILED DESCRIPTION OF THE PREFERRED EMBODIMENTS

Figure 1A:
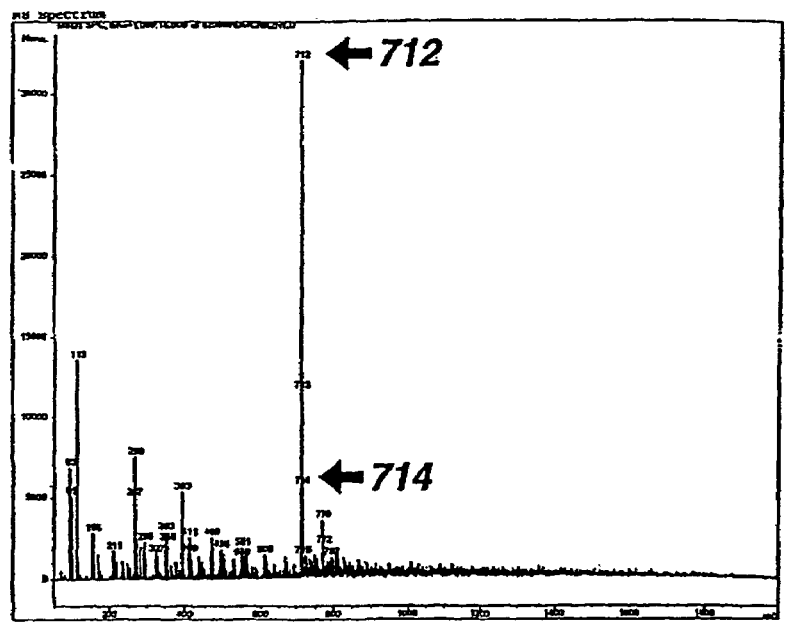
FIGS. 1A-1B—The ES-MS analysis of synthetic p6.1 peptide (FIG. 1A), and biotinylated synthetic p6.1 (FIG. 1B). Arrows, major peaks corresponding to molecular mass of the oxidized p6.1 monomer (712), reduced p6.1 monomer (714), oxidized biotinylated p6.1 monomer (938), and reduced biotinylated p6. 1 monomer (940).

As discussed above, overexpression of ErbB-2 is associated with increased rates of tumor growth and enhanced rates of metastases (Hynes and Stern, 1994). The relatively high levels of ErbB-2 in many human malignancies, along with its extracellular accessibility, make it an attractive target for the development of tumor-specific agents. Herceptin™, a humanized monoclonal antibody against ErbB-2 (Baselga et al., 1998), has recently been approved for the treatment of metastatic breast cancer. Unfortunately, this reagent was found to aggravate doxorubicin-induced cardiac dysfunction and, possibly, be cardiotoxic on its own (Piccart, 1999).

Peptides, in contrast to large molecules like antibodies, are known to exhibit less toxicity and possess better pharmacokinetic properties such as higher target-to-background ratios and faster blood clearance (Fischman et al., 1993). Advances in powerful combinatorial technologies, such as the use of bacteriophage display libraries, permit the rapid screening of large peptide libraries for binding to a particular antigen or receptor. A number of peptides that bind receptor molecules (Doorbar and Winter, 1994), oncoproteins (Renschler et al., 1995), integrins (Murayama et al., 1996), and tumor-associated carbohydrates (Peletskaya et al., 1997, Peletskaya et al., 1996) have been identified using bacteriophage display libraries. Bacteriophage display technology has also been employed to optimize binding affinities of heregulin variants for the ErbB3 receptor (Ballinger et al., 1998) and to study binding interactions of the heregulin-P EGF domain with ErbB3 and ErbB4 (Jones et al., 1998). The present inventors, using this approach, attempted to identify peptides that specifically and tightly bound the extracellular domain (ECD) of human ErbB-2.

The inventors identified three peptides from a bacteriophage display library using affinity selection against recombinant ECD of human ErbB-2 (ErbB-2-ECD). One of the isolated peptides, KCCYSL (p6.1), represented 75% of selected population and exhibited limited linear homology with several proteins that potentially could interact with ErbB-1 receptor. Sequence analysis suggested that the p6.1 peptide may also act as a mimetic of a CCY/F motif present in the EGF-like domain of all known ErbB ligands. The 6-amino acid p6.1 peptide was chemically synthesized and examined for its binding affinities and specificities. Results from the binding studies showed that the synthetic p6.1 peptide specifically recognized the recombinant ErbB-2-ECD, the ErbB-1 receptor protein, and human breast and prostate cancer cells overexpressing ErbB-2. In conclusion, the results demonstrate that the peptide p6.1, identified from a random peptide phage display library, is capable of specific interaction with oncogenically activated members of the ErbB growth factor receptor family. The p6.1 peptide can thus be used as a vehicle for specific delivery of labels and agents to cancer cells for therapeutic and diagnostic purposes.

A. ErbB-2 and ErbB-2 Cancers

The c-erbB gene encodes the epidermal growth factor receptor (EGFr) and is highly homologous to the transforming gene of the avian erythroblastosis virus (Downward et al., 1984). The c-erbB gene is a member of the tyrosine-specific protein kinase family to which many proto-oncogenes belong. The c-erbB gene has recently been found to be similar, but distinct from, an oncogene referred to variously as ErbB-2, HER-2 or neu oncogene, now known to be intimately involved in the pathogenesis of a number of cancers.

The ErbB-2 gene, which encodes a p185 tumor antigen, was first identified in transfection studies in which NIH 3T3 cells were transfected with DNA from chemically induced rat neuroglioblastomas (Shih et al., 1981). The p185 protein has an extracellular, transmembrane, and intracellular domain, and therefore has a structure consistent with that of a growth factor receptor (Schechter et al., 1984). The human ErbB-2 gene was first isolated due to its homology with v-erbB and EGF-r probes.

The ErbB-2 oncogene is of particular importance to medical science because its presence is correlated with the incidence of cancers of the human breast and female genital tract. Moreover, amplification/overexpression of this gene has been directly correlated with relapse and survival in human breast cancer (Slamon et al., 1987).

B. Peptides and Peptide Conjugates

The present invention focuses on peptides comprising the sequence KCCYSL, designated p6.1. p6.1 selected from random 6-amino acid phage peptide library, exhibited specific binding activity to recombinant ErbB-2-ECD and to human cancer cells expressing ErbB-2 receptor. Remarkably, the disulfide constrained p6.1 peptide was derived from an unconstrained random peptide library. So far, only a few unconstrained libraries have yielded putative disulfide constrained sequences (Devlin et al., 1990, Kay et al., 1993). Most of the reported disulfide-containing peptides have been derived from libraries comprised of constrained peptides by design (Giebel et al., 1995, Oldenburg et al., 1992, Wrighton et al., 1996).

In this study, the inventors used a library with random peptides inserted near the N-terminus of the mature M13 viral pIII protein. There are eight cysteine residues in the mature pIII molecule. Since the phage particles are maintained in an oxidizing environment, one can reasonably suggest that two cysteines of the p6.1 insert could be disulfide-bonded not only with each other, but with the cysteines of the pIII protein as well. The latter, however, would likely interfere with the pIII structure resulting in a reduction of phage infectivity and under-presentation of the clone in the library. Thus, the inventors believe that the cysteine residues of p6.1 displayed on the phage surface participate in disulfide bond formation within the peptide insert. Nevertheless, there is a possibility that the insert may exist in a reduced linear form on the surface of the phage.

Synthetic p6.1 exhibited binding activity not only to ErbB-2, but also to another member of the ErbB receptor family, ErbB-1. This result supported that of an overall 40-50% homology between ErbB-2 and ErbB-1. The inventors suggest that the binding activity of p6.1 peptide toward both ErbB-2 and ErbB-1 is related to its constrained nature. The oxidized form of p6.1 (FIG. 3B) could mimic a CC(Y/F) motif, found in the structure of the EGF-like domain of all known ErbB ligands (FIG. 3C). The CC(Y/F) motif is formed due to the $C_{14}$-$C_{31}$, (EGF numbering). disulfide bridge (FIG. 3A). The residues participating in the formation of this motif, two cysteines and a semi-conservative aromatic amino acid (Y/F), are invariant in all of the ErbB family ligands (FIG. 3C). Such invariance suggests the importance of these amino acids in defining either a structure or the binding properties of the EGF-like proteins. Phenylalanine from the CCF motif of TGF-α was shown to appear on its binding interface (McInnes and Sykes, 1997). Remarkably, another EGF-like polypeptide, Cripto-1, which is not known to bind any of the ErbB-2 receptors, does not contain CCY/F motif in its structure.

Having identified a key structure in ErbB receptor-binding, the inventors also contemplated that variants of the KCCYSL sequence may be employed. For example, certain non-natural amino acids that satisfy the structural constraints of the KCCYSL sequence may be substituted without a loss, and perhaps with an improvement in, biological function, i.e., ErbB-2 binding.

In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

1. Peptide Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

2. Linking Agents

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various agents can be covalently bound to peptides through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have linked by established procedures. The inclusion of PE in the liposome provides an active functional residue, a primary amine, on the liposomal surface for cross-linking purposes. ST peptides are bound covalently to discrete sites on the liposome surfaces. The number and surface density of these sites will be dictated by the liposome formulation and the liposome type. The liposomal surfaces may also have sites for non-covalent association. To form covalent conjugates of peptides and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. Table 1 details certain hetero-bifunctional cross-linkers considered useful in the present invention.

TABLE 1

HETERO-BIFUNCTIONAL CROSS-LINKERS

| Linker | Reactive Toward | Advantages and Applications | Spacer Arm Length/ after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |

TABLE 1-continued

HETERO-BIFUNCTIONAL CROSS-LINKERS

| Linker | Reactive Toward | Advantages and Applications | Spacer Arm Length/ after cross-linking |
|---|---|---|---|
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

In instances where a particular peptide does not contain a residue amenable for a given cross-linking reagent in its native sequence, conservative genetic or synthetic amino acid changes in the primary sequence can be utilized.

3. Diagnostic Agents

In accordance with the present invention, there are provided diagnostic methods for detecting cancer cells. Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, bismuth$^{211}$, bismuth$^{213}$ and/or yttrium$^{90}$. Of particular interest are lutetium$^{177}$, samarium$^{153}$, holmium$^{166}$ and actinium$^{225}$. Also, see Table 6, attached. Radioactively labeled ST peptides of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. ST peptides according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

4. Therapeutic Agents

The present invention also provides for the delivery of therapeutic agents to cancer cells using ST peptides to target such agents. The agents may be linked directly to the peptide (above), or they may be encapsulated in a liposome (below) which, in turn, is targeted by the ST peptide. Some examples of therapeutic agents are discussed in the following pages.

a. Radiopharmaceuticals

A number of different radioactive substances can be used in cancer therapy. Examples of radioactive isotopes for therapeutic applications include astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, lutetium$^{177}$, samarium$^{153}$, holmium$^{166}$, bismuth$^{212}$, bismuth$^{213}$ and actinium$^{225}$.

b. Chemopharmaceuticals

The term "chemotherapy" refers to the use of drugs to treat cancer. A "chemotherapeutic agent" is used to connote a compound or composition that is administered in the treatment of cancer. One subtype of chemotherapy known as biochemotherapy involves the combination of a chemotherapy with a biological therapy.

Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, hormone agents, miscellaneous agents, and any analog or derivative variant thereof Chemotherapeutic agents and methods of administration, dosages, etc. are well known to those of skill in the art (see for example, the Goodman & Gilman's "The Pharmacological Basis of Therapeutics" and in "Remington's Pharmaceutical Sciences", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

i. Alkylating agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat, for example, chronic leukemia, non-Hodgkin's lymphoma, Hodgkin's disease, multiple myeloma, and particular cancers of the breast, lung, and ovary. An alkylating agent, may include, but is not limited to, a nitrogen mustard, an ethylenimene, a methylmelamine, an alkyl sulfonate, a nitrosourea or a triazines.

They include but are not limited to: busulfan, chlorambucil, cisplatin, cyclophosphamide (cytoxan), dacarbazine, ifosfamide, mechlorethamine (mustargen), and melphalan. In specific aspects, troglitazaone can be used to treat cancer in combination with any one or more of these alkylating agents, some of which are discussed below.

1. Nitrogen Mustards

A nitrogen mustard may be, but is not limited to, mechlorethamine ($HN_2$), which is used for Hodgkin's disease and non-Hodgkin's lymphomas; cyclophosphamide and/or ifosfamide, which are used in treating such cancers as acute or chronic lymphocytic leukemias, Hodgkin's disease, non-Hodgkin's lymphomas, multiple myeloma, neuroblastoma, breast, ovary, lung, Wilm's tumor, cervix testis and soft tissue sarcomas; melphalan (L-sarcolysin), which has been used to treat such cancers as multiple myeloma, breast and ovary; and chlorambucil, which has been used to treat diseases such as, for example, chronic lymphatic (lymphocytic) leukemia, malignant lymphomas including lymphosarcoma, giant follicular lymphoma, Hodgkin's disease and non-Hodgkin's lymphomas.

a. Chlorambucil

Chlorambucil (also known as leukeran) is a bifunctional alkylating agent of the nitrogen mustard type that has been found active against selected human neoplastic diseases. Chlorambucil is known chemically as 4-[bis(2-chlorethyl) amino] benzenebutanoic acid.

Chlorambucil is available in tablet form for oral administration. It is rapidly and completely absorbed from the gastrointestinal tract. For example, after a single oral doses of about 0.6 mg/kg to about 1.2 mg/kg, peak plasma chlorambucil levels are reached within one hour and the terminal half-life of the parent drug is estimated at about 1.5 hours. About 0.1 mg/kg/day to about 0.2 mg/kg/day or about 3 6 mg/m$^2$/day to about 6 mg/m$^2$/day or alternatively about 0.4 mg/kg may be used for antineoplastic treatment. Chlorambucil is not curative by itself but may produce clinically useful palliation.

b. Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [$(ClCH_2CH_2)2N$—$POCl_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable oral doses for adults include, for example, about 1 mg/kg/day to about 5 mg/kg/day (usually in combination), depending upon gastrointestinal tolerance; or about 1 mg/kg/day to about 2 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. In some aspects, a dose of about 250 mg/kg/day may be administered as an antineoplastic. Because of gastrointestinal adverse effects, the intravenous route is preferred for loading. During maintenance, a leukocyte count of about 3000/mm$^3$ to 4000/mm$^3$ usually is desired. The drug also sometimes is administered intramuscularly, by infiltration or into body cavities. It is available in dosage forms for injection of about 100 mg, about 200 mg and about 500 mg, and tablets of about 25 mg and about 50 mg.

c. Melphalan

Melphalan, also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis (2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKal of about 2.1. Melphalan is available in tablet form for oral administration and has been used to treat multiple myeloma. Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of about 0.2 mg/kg daily for five days as a single course. Courses are repeated about every four to five weeks depending upon hematologic tolerance (Smith and Rutledge, 1975; Young et al., 1978). Alternatively in certain embodiments, the dose of melphalan used could be as low as about 0.05 mg/kg/day or as high as about 3 mg/kg/day or greater.

2. Ethylenimenes and Methymelamines

An ethyleninene and/or a methylmelamine include, but are not limited to, hexamethylmelamine, used to treat ovary cancer; and thiotepa, which has been used to treat bladder, breast and ovary cancer.

3. Alkyl Sulfonates

An alkyl sulfonate includes but is not limited to such drugs as busulfan, which has been used to treat chronic granulocytic leukemia.

Busulfan (also known as myleran) is a bifunctional alkylating agent. Busulfan is known chemically as 1,4-butanediol dimethanesulfonate. Busulfan is available in tablet form for oral administration, wherein for example, each scored tablet contains about 2 mg busulfan and the inactive ingredients magnesium stearate and sodium chloride.

Busulfan is indicated for the palliative treatment of chronic myelogenous (myeloid, myelocytic, granulocytic) leukemia Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. Busulfan has been shown to be superior to splenic irradiation with respect to survival times and maintenance of hemoglobin levels, and to be equivalent to irradiation at controlling splenomegaly.

4. Nitrosourea

Nitrosureas, like alkylating agents, inhibit DNA repair proteins. They are used to treat non-Hodgkin's lymphomas, multiple myeloma, malignant melanoma, in addition to brain tumors. A nitrosourea include but is not limited to a carmustine (BCNU), a lomustine (CCNU), a semustine (methyl-CCNU) or a streptozocin. Semustine has been used in such cancers as a primary brain tumor, a stomach or a colon cancer. Stroptozocin has been used to treat diseases such as a malignant pancreatic insulinoma or a malignant carcinoid. Streptozocin has been used to treat such cancers as a malignant melanoma, Hodgkin's disease and soft tissue sarcomas.

a. Carmustine

Carmustine (sterile carmustine) is one of the nitrosoureas used in the treatment of certain neoplastic diseases. It is 1,3 bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has been used in treating such cancers as a multiple myeloma or a malignant melanoma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

Sterile carmustine is commonly available in 100 mg single dose vials of lyophilized material. The recommended dose of carmustine as a single agent in previously untreated patients is about 150 mg/m$^2$ to about 200 mg/m$^2$ intravenously every 6 weeks. This may be given as a single dose or divided into daily injections such as about 75 mg/m$^2$ to about 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention, for example about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$ to about 100 mg/m$^2$.

b. Lomustine

Lomustine is one of the nitrosoureas used in the treatment of certain neoplastic diseases. It is 1-(2-chloro-ethyl)-3-cyclohexyl-1 nitrosourea It is a yellow powder with the empirical formula of $C_9H_{16}ClN_3O_2$ and a molecular weight of 233.71. Lomustine is soluble in 10% ethanol (about 0.05 mg/mL) and in absolute alcohol (about 70 mg/mL). Lomustine is relatively insoluble in water (less than about 0.05 mg/mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from about 30 mg/m$^2$ to 100 mg/m$^2$, about half of the radioactivity given was excreted in the form of degradation products within 24 hours. The serum half-life of the metabolites ranges from about 16 hours to about 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. Lomustine has been used to treat such cancers as small-cell lung cancer. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is about 130 mg/m$^2$ as a single oral dose every 6 weeks. In individuals with compromised bone marrow function, the dose should be reduced to about 100 mg/m$^2$ every 6 weeks. When lomustine is used in combination with other myelosuppressive drugs, the doses should be adjusted accordingly. It is understood that other doses may be used for example, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$ to about 120 mg/m$^2$.

C. Triazine

A triazine include but is not limited to such drugs as a dacabazine (DTIC; dimethyltriazenoimidaz olecarboxamide), used in the treatment of such cancers as a malignant melanoma, Hodgkin's disease and a soft-tissue sarcoma.

ii. Antimetabolites

Antimetabolites disrupt DNA and RNA synthesis. Unlike alkylating agents, they specifically influence the cell cycle during S phase. They have used to combat chronic leukemias in addition to tumors of breast, ovary and the gastrointestinal tract. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

1. Folic Acid Analogs

Folic acid analogs include but are not limited to compounds such as methotrexate (amethopterin), which has been used in the treatment of cancers such as acute lymphocytic leukemia, choriocarcinoma, mycosis fungoides, breast, head and neck, lung and osteogenic sarcoma.

2. Pyrimidine Analogs

Pyrimidine analogs include such compounds as cytarabine (cytosine arabinoside), 5-fluorouracil (fluouracil; 5-FU) and floxuridine (fluorode-oxyuridine; FudR). Cytarabine has been used in the treatment of cancers such as acute granulocytic leukemia and acute lymphocytic leukemias. Floxuridine and 5-fluorouracil have been used in the treatment of cancers such as breast, colon, stomach, pancreas, ovary, head and neck, urinary bladder and topical premalignant skin lesions.

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

3. Purine Analogs and Related Inhibitors

Purine analogs and related compounds include, but are not limited to, mercaptopurine (6-mercaptopurine; 6-MP), thioguanine (6-thioguanine; TG) and pentostatin (2-deoxycoformycin). Mercaptopurine has been used in acute lymphocytic, acute granulocytic and chronic granulocytic leukemias. Thrioguanine has been used in the treatment of such cancers as acute granulocytic leukemia, acute lymphocytic leukemia and chronic lymphocytic leukemia. Pentostatin has been used in such cancers as hairy cell leukemias, mycosis fungoides and chronic lymphocytic leukemia.

c. Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

i. Mitotic Inhibitors

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

1. Epipodophyllotoxins

Epipodophyllotoxins include such compounds as teniposide and VP16. VP16 is also known as etoposide and is used primarily for treatment of testicular tumors, in combination with bleomycin and cisplatin, and in combination with cisplatin for small-cell carcinoma of the lung. Teniposide and VP16 are also active against cancers such as testis, other lung cancer, Hodgkin's disease, non-Hodgkin's lymphomas, acute granulocytic leukemia, acute non-lymphocytic leukemia, carcinoma of the breast, and Kaposi's sarcoma associated with acquired immunodeficiency syndrome (AIDS).

VP16 is available as a solution (e.g., 20 mg/ml) for intravenous administration and as 50 mg, liquid-filled capsules for oral use. For small-cell carcinoma of the lung, the intravenous dose (in combination therapy) can be as much as about 100 mg/m$^2$ or as little as about 2 mg/m$^2$, routinely about 35 mg/m$^2$, daily for about 4 days, to about 50 mg/m$^2$, daily for about 5 days have also been used. When given orally, the dose should be doubled. Hence the doses for small cell lung carcinoma may be as high as about 200 mg/m$^2$ to about 250 mg/m$^2$. The intravenous dose for testicular cancer (in combination therapy) is about 50 mg/m$^2$ to about 100 mg/m$^2$ daily for about 5 days, or about 100 mg/m$^2$ on alternate days, for three doses. Cycles of therapy are usually repeated about every 3 to 4 weeks. The drug should be administered slowly (e.g. about 30 minutes to about 60 minutes) as an infusion in order to avoid hypotension and bronchospasm, which are probably due to the solvents used in the formulation.

2. Taxoids

Taxoids are a class of related compounds isolated from the bark of the ash tree, *Taxus brevifolia*. Taxoids include but are not limited to compounds such as docetaxel and paclitaxel.

Paclitaxel binds to tubulin (at a site distinct from that used by the vinca alkaloids) and promotes the assembly of microtubules. Paclitaxel is being evaluated clinically; it has activity against malignant melanoma and carcinoma of the ovary. In certain aspects, maximal doses are about 30 mg/m$^2$ per day for about 5 days or about 210 mg/mm$^2$ to about 250 mg/m$^2$ given once about every 3 weeks.

3. Vinca Alkaloids

Vinca alkaloids are a type of plant alkaloid identified to have pharmaceutical activity. They include such compounds as vinblastine (VLB) and vincristine. Vinblastine is an example of a plant alkaloid that can be used for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. When the drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in about 7 days to about 10 days. If a moderate level of leukopenia (approximately 3000 cells/mm$^3$) is not attained, the weekly dose may be increased gradually by increments of about 0.05 mg/kg of body weight. In regimens designed to cure testicular cancer, vinblastine is used in doses of about 0.3 mg/kg about every 3 weeks irrespective of blood cell counts or toxicity.

An important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, testis cancer, neuroblastoma, and Letterer-Siwe disease (bistiocytosis X), as well as in carcinoma of the breast and choriocarcinoma in women.

Doses of about 0.1 mg/kg to about 0.3 mg/kg can be administered or about 1.5 mg/m$^2$ to about 2 mg/m$^2$ can also be administered. Alternatively, about 0.1 mg/m$^2$, about 0.12 mg/m$^2$, about 0.14 mg/m$^2$, about 0.15 mg/m$^2$, about 0.2 mg/m$^2$, about 0.25 mg/m$^2$, about 0.5 mg/m$^2$, about 1.0 mg/m$^2$, about 1.2 mg/m$^2$, about 1.4 mg/m$^2$, about 1.5 mg/m$^2$, about 2.0 mg/m$^2$, about 2.5 mg/m$^2$, about 5.0 mg/m$^2$, about 6 mg/m$^2$, about 8 mg/m$^2$, about 9 mg/m$^2$, about 10 mg/m$^2$, to about 20 mg/m$^2$, can be given.

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is about 0.4 mM.

Vinblastine and vincristine bind to plasma proteins. They are extensively concentrated in platelets and to a lesser extent in leukocytes and erythrocytes. Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than about 3 mg/dl (about 50 mM).

Vincristine sulfate is available as a solution (e.g., 1 mg/ml) for intravenous injection. Vincristine used together with corticosteroids is presently the treatment of choice to induce remissions in childhood leukemia; the optimal dosages for these drugs appear to be vincristine, intravenously, about 2 mg/m$^2$ of body-surface area, weekly; and prednisone, orally, about 40 mg/m$^2$, daily. Adult patients with Hodgkin's disease or non-Hodgkin's lymphomas usually receive vincristine as a part of a complex protocol. When used in the MOPP regimen, the recommended dose of vincristine is about 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, small cell lung, and carcinomas of the breast, bladder, and the male and female reproductive systems.

Doses of vincristine include about 0.01 mg/kg to about 0.03 mg/kg or about 0.4 mg/m$^2$ to about 1.4 mg/m$^2$ can be administered or about 1.5 mg/m$^2$ to about 2 mg/m$^2$ can also be administered. Alternatively, in certain embodiments, about 0.02 mg/m$^2$, about 0.05 mg/m$^2$, about 0.06 mg/m$^2$, about 0.07 mg/m$^2$, about 0.08 mg/m$^2$, about 0.1 mg/m$^2$, about 0.12 mg/m$^2$, about 0.14 mg/m$^2$, about 0.15 mg/m$^2$, about 0.2 mg/m$^2$, about 0.25 mg/m$^2$ can be given as a constant intravenous infusion.

ii. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include, but are not limited to, bleomycin, dactinomycin, daunorubicin, doxorubicin (Adriamycin), plicamycin (mithramycin) and idarubicin. Widely used in clinical setting for the treatment of neoplasms these compounds generally are administered through intravenous bolus injections or orally.

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of diseases including ovarian, endometrial and breast tumors, bronchogenic oat-cell carcinoma, non-small cell lung carcinoma, stomach, genitourinary, thyroid, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma, soft tissue sarcoma, Ewing's sarcoma, rhabdomyosarcoma and acute lymphocytic leukemia. It is an alternative drug for the treatment of other diseases such as islet cell, cervical, testicular and adrenocortical cancers. It is also an immunosuppressant.

Doxorubicin is absorbed poorly and is preferably administered intravenously. The pharmacokinetics are multicompartmental. Distribution phases have half-lives of 12 minutes and 3.3 hours. The elimination half-life is about 30 hours, with about 40% to about 50% secreted into the bile. Most of the remainder is metabolized in the liver, partly to an active metabolite (doxorubicinol), but a few percent is excreted into the urine. In the presence of liver impairment, the dose should be reduced.

In certain embodiments, appropriate intravenous doses are, adult, about 60 mg/m² to about 75 mg/m² at about 21-day intervals or about 25 mg/m² to about 30 mg/m² on each of 2 or 3 successive days repeated at about 3 week to about 4 week intervals or about 20 mg/m² once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by about 50% if the serum bilirubin lies between about 1.2 mg/dL and about 3 mg/dL and by about 75% if above about 3 mg/dL. The lifetime total dose should not exceed about 550 mg/m² in patients with normal heart function and about 400 mg/m² in persons having received mediastinal irradiation. In certain embodiments, and alternative dose regiment may comprise about 30 mg/m² on each of 3 consecutive days, repeated about every 4 week. Exemplary doses may be about 10 mg/m², about 20 mg/m², about 30 mg/m², about 50 mg/m², about 100 mg/m², about 150 mg/m², about 175 mg/m², about 200 mg/m², about 225 mg/m², about 250 mg/m², about 275 mg/m², about 300 mg/m², about 350 mg/m², about 400 mg/m², about 425 mg/m², about 450 mg/m², about 475 mg/m², to about 500 mg/m².

Daunorubicin hydrochloride, 5,12-Naphthacenedione, (8S-cis)-8-acetyl-10-[(3-amino-2,3,6-trideoxy-a-lyxo-hexanopyranosyl)oxy]-7,8,9,10-tetrahydro-6,8,11-trihydroxy-10-methoxy-, hydrochloride; also termed cerubidine and available from Wyeth. Daunorubicin (daunomycin; rubidomycin) intercalates into DNA, blocks DAN-directed RNA polymerase and inhibits DNA synthesis. It can prevent cell division in doses that do not interfere with nucleic acid synthesis.

In combination with other drugs it is often included in the first-choice chemotherapy of diseases such as, for example, acute granulocytic leukemia, acute myelocytic leukemia in adults (for induction of remission), acute lymphocytic leukemia and the acute phase of chronic myelocytic leukemia. Oral absorption is poor, and it preferably given by other methods (e.g., intravenously). The half-life of distribution is 45 minutes and of elimination, about 19 hours. The half-life of its active metabolite, daunorubicinol, is about 27 hours. Daunorubicin is metabolized mostly in the liver and also secreted into the bile (about 40%). Dosage must be reduced in liver or renal insufficiencies.

Generally, suitable intravenous doses are (base equivalent): adult, younger than 60 years, about 45 mg/m²/day (about 30 mg/m² for patients older than 60 year) for about 1 day, about 2 days or about 3 days about every 3 weeks or 4 weeks; or about 0.8 mg/kg/day for about 3 days, about 4 days, about 5 days to about 6 days about every 3 weeks or about 4 weeks; no more than about 550 mg/m² should be given in a lifetime, except only about 450 mg/m² if there has been chest irradiation; children, about 25 mg/m² once a week unless the age is less than 2 years or the body surface less than about 0.5 m, in which case the weight-based adult schedule is used. It is available in injectable dosage forms (base equivalent) of about 20 mg (as the base equivalent to about 21.4 mg of the hydrochloride). Exemplary doses may be about 10 mg/m², about 20 mg/m², about 30 mg/m², about 50 mg/m², about 100 mg/m², about 150 mg/m², about 175 mg/m², about 200 mg/m², about 225 mg/m², about 250 mg/m², about 275 mg/m², about 300 mg/m², about 350 mg/m², about 400 mg/m², about 425 mg/m², about 450 mg/m², about 475 mg/m², to about 500 mg/m².

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed. Mitomycin has been used in tumors such as stomach, cervix, colon, breast, pancreas, bladder and head and neck.

In humans, mitomycin is rapidly cleared from the serum after intravenous administration. Time required to reduce the serum concentration by about 50% after a 30 mg bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D (Dactinomycin) [50-76-0]; $C_{62}H_{86}N_{12}O_{16}$ (1255.43) is an antineoplastic drug that inhibits DNA-dependent RNA polymerase. It is often a component of first-choice combinations for treatment of diseases such as, for example, choriocarcinoma, embryonal rhabdomyosarcoma, testicular tumor, Kaposi's sarcoma and Wilms' tumor. Tumors that fail to respond to systemic treatment sometimes respond to local perfusion. Dactinomycin potentiates radiotherapy. It is a secondary (efferent) immunosuppressive.

In certain specific aspects, actinomycin D is used in combination with agents such as, for example, primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hours. The drug does not pass the blood-brain barrier. Actinomycin D is supplied as a lyophilized powder (0/5 mg in each vial). The usual daily dose is about 10 mg/kg to about 15 mg/kg; this is given intravenously for about 5 days; if no manifestations of toxicity are encountered, additional courses may be given at intervals of about 3 weeks to about 4 weeks. Daily injections of about 100 mg to about 400 mg have been given to children for about 10 days to about 14 days; in other regimens, about 3 mg/kg to about 6 mg/kg, for a total of about 125 mg/kg, and weekly maintenance doses of about 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be about 100 mg/m$^2$, about 150mg/m$^2$, about 175mg/m$^2$, about 200mg/m$^2$, about 225mg/m$^2$, about 250mg/m$^2$, about 275mg/m$^2$, about 300mg/m$^2$, about 350mg/m$^2$, about 400mg/m$^2$, about 425 mg/m$^2$, about 450 mg/m$^2$, about 475 mg/m$^2$, to about 500 mg/m$^2$.

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of greater than about 35 mL per minute, the serum or plasma terminal elimination half-life of bleomycin is approximately 115 minutes. In patients with a creatinine clearance of less than about 35 mL per minute, the plasma or serum terminal elimination half-life increases exponentially as the creatinine clearance decreases. In humans, about 60% to about 70% of an administered dose is recovered in the urine as active bleomycin. In specific embodiments, bleomycin may be given by the intramuscular, intravenous, or subcutaneous routes. It is freely soluble in water. Because of the possibility of an anaphylactoid reaction, lymphoma patients should be treated with two units or less for the first two doses. If no acute reaction occurs, then the regular dosage schedule may be followed.

In preferred aspects, bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), esophagus, lung and genitourinary tract, Hodgkin's disease, non-Hodgkin's lymphoma, skin, penis, cervix, and vulva. It has also been used in the treatment of lymphomas and testicular carcinoma.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

d. Miscellaneous Agents

Some chemotherapy agents do not qualify into the previous categories based on their activities. They include, but are not limited to, platinum coordination complexes, anthracenedione, substituted urea, methyl hydrazine derivative, adrenalcortical suppressant, amsacrine, L-asparaginase, and tretinoin. It is contemplated that they are included within the compositions and methods of the present invention for use in combination therapies.

i. Platinum Coordination Complexes

Platinum coordination complexes include such compounds as carboplatin and cisplatin (cis-DDP). Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes, such as for example, intravenous, subcutaneous, intratumoral or intraperitoneal injection. Cisplatin can be used alone or in combination with other agents, with efficacious doses used in clinical applications of about 15 mg/m$^2$ to about 20 mg/m$^2$ for 5 days every three weeks for a total of three courses being contemplated in certain embodiments. Doses may be, for example, about 0.50 mg/m$^2$, about 1.0 mg/m$^2$, about 1.50 mg/m$^2$, about 1.75 mg/m$^2$, about 2.0 mg/m$^2$, about 3.0 mg/m$^2$, about 4.0 mg/m$^2$, about 5.0 mg/m$^2$, to about 10 mg/m$^2$.

ii. Other Agents

An anthracenedione such as mitoxantrone has been used for treating acute granulocytic leukemia and breast cancer. A substituted urea such as hydroxyurea has been used in treating chronic granulocytic leukemia, polycythemia vera, thrombocytosis and malignant melanoma. A methyl hydrazine derivative such as procarbazine (N-methylhydrazine, MIH) has been used in the treatment of Hodgkin's disease. An adrenocortical suppressant such as mitotane has been used to treat adrenal cortex cancer, while aminoglutethimide has been used to treat Hodgkin's disease.

e. Toxins

Various toxins are also useful in the treatment of cancers. As part of the present invention, toxins such as ricin A-chain (Burbage, 1997), diphtheria toxin A (Massuda et al., 1997; Lidor, 1997), pertussis toxin A subunit, *E. coli* enterotoxin toxin A subunit, cholera toxin A subunit and *Pseudomonas* toxin c-terminal are suitable. It has demonstrated that transfection of a plasmid containing the fusion protein regulatable diphtheria toxin A chain gene was cytotoxic for cancer cells.

f. Gene Therapy Vectors

Tumor cell resistance to agents, such as chemotherapeutic and radiotherapeutic agents, represents a major problem in clinical oncology. One goal of current cancer research is to find ways to improve the efficacy of one or more anti-cancer agents by combining such an agent with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that gene therapy could be enhanced by specific cell targeting afforded by ST peptides, as discussed below.

i. Inducers of Cellular Proliferation

In one embodiment of the present invention, it is contemplated that antisense mRNA directed to a particular inducer of cellular proliferation is used to prevent expression of the inducer of cellular proliferation. The proteins that induce cellular proliferation further fall into various categories dependent on function. The commonality of all of these proteins is their ability to regulate cellular proliferation.

For example, a form of PDGF, the sis oncogene, is a secreted growth factor. Oncogenes rarely arise from genes encoding growth factors, and at the present, sis is the only known naturally-occurring oncogenic growth factor.

The largest class of oncogenes includes the signal transducing proteins (e.g. Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

Other proteins such as Jun, Fos and Myc are proteins that directly exert their effects on nuclear functions as transcription factors.

ii. Inhibitors of Cellular Proliferation

In certain embodiments, the restoration of the activity of an inhibitor of cellular proliferation through a genetic construct is contemplated. Tumor suppressor oncogenes function to inhibit excessive cellular proliferation. The inactivation of these genes destroys their inhibitory activity, resulting in unregulated proliferation. The tumor suppressors Rb, p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by-an inhibitory subunit, the p16$^{INK4}$ has been biochemically characterized as a protein that specifically binds to and inhibits CDK4, and thus may regulate Rb phosphorylation (Serrano et al., 1993; Serrano et al., 1995). Since the p16$^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p19, $p_{21}{}^{WAF1}$, and $p27^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, antithrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

iii. Regulators of Programmed Cell Death

In certain embodiments, it is contemplated that genetic constructs that stimulate apoptosis will be used to promote the death of diseased or undesired tissue. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g. Bcl$_{XL}$, Bcl$_W$, Bcl$_S$, Mcl-1, A1, Bfl-1) or counteract Bcl-2 function and promote cell death (e.g. Bax, Bak, Bik, Bim, Bid, Bad, Harakiri).

g. Immunotherapy

An immunotherapeutic agent generally triggers immune effector cells and molecules to target and destroy cancer cells.

The immune effector may be, for example, an antibody specific for some marker on the surface of a tumor cell. The antibody alone may serve as an effector of therapy or it may recruit other cells to actually effect cell killing. Various effector cells include cytotoxic T cells and NK cells.

i. Immune Stimulators

A specific aspect of immunotherapy is to use an immune stimulating molecule as an agent, or more preferably in conjunction with another agent, such as for example, a cytokines such as for example IL2, IL-4, IL-12, GM-CSF, tumor necrosis factor; interferons alpha, beta, and gamma; F42K and other cytokine analogs; a chemokine such as for example MIP-1, MIP-1β, MCP-1, RANTES, IL-8; or a growth factor such as for example FLT3 ligand.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by γ-interferon, so that the combination potentially is dangerous. A hybrid of TNF and interferon-α also has been found to possess anti-cancer activity.

Another cytokine specifically contemplate is interferon α. Interferon α has been used in treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

ii. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991). In melanoma immunotherapy, those patients who elicit high IgM response often survive better than those who elicit no or low IgM antibodies. IgM antibodies are often transient antibodies and the exception to the rule appears to be anti-ganglioside or anticarbohydrate antibodies.

iii. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

h. Hormonal Therapy

Hormonal therapy may also be used in conjunction with the present invention and in combination with any other cancer therapy or agent(s). The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

i. Adrenocorticosteroids

Corticosteroid hormones are useful in treating some types of cancer (e.g. non-Hodgkin's lymphoma, acute and chronic lymphocytic leukemias, breast cancer, and multiple myeloma). Though these hormones have been used in the treatment of many non-cancer conditions, they are considered chemotherapy drugs when they are implemented to kill or slow the growth of cancer cells. Corticosteroid hormones can increase the effectiveness of other chemotherapy agents, and consequently, they are frequently used in combination treatments. Prednisone and dexamethasone are examples of corticosteroid hormones.

ii. Other Hormones and Antagonists

Progestins such as hydroxyprogesterone caproate, medroxyprogesterone acetate, and megestrol acetate have been used in cancers of the endometrium and breast. Estrogens such as diethylstilbestrol and ethinyl estradiol have been used in cancers such as breast and prostate. Anti-estrogens such as tamoxifen have been used in cancers such as breast. Androgens such as testosterone propionate and fluoxymesterone have also been used in treating breast cancer. Anti-androgens such as flutamide have been used in the treatment of prostate cancer. Gonadotropin-releasing hormone analogs such as leuprolide have been used in treating prostate cancer.

C. Combination Therapies

Multidrug resistance (MDR) in cancer cells represents a major problem in clinical. medicine. One goal of current research is to find ways to overcome such resistance. In addition, drug combinations are known to reduce the dosages required, and in some cases, produce synergistic effects. Thus, in order to increase the effectiveness of peptide-based therapies described herein, it may be desirable to combine these compositions with other agents effective in the treatment of cancer. A therapeutic agent is capable of negatively affecting cancer cell growth in a subject, for example, by killing cancer cells, reducing the growth rate of cancer cells, or otherwise increasing the quality of life of the afflicted subject. This process may involve contacting the subject with the peptide/agent and the second therapy at the same time. This may be achieved by contacting the cell with a single composition or pharmacological formulation that includes both the peptide/agent and the second therapy, or by contacting the cell with two distinct compositions or formulations, at the same time, wherein one composition includes the peptide/agent and the other includes the second agent.

Alternatively, the peptide/agent therapy may precede or follow the second therapy by intervals ranging from minutes to weeks. In embodiments where the other agent and peptide/agent are applied separately to the cell, one would generally ensure that a significant period of time did not expire between the time of each delivery, such that the second agent and peptide/agent would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, peptide/agent therapy is "A" and the secondary agent is "B":

```
A/B/A  B/A/B  B/B/A  A/A/B  A/B/B  B/A/A  A/B/B/B  B/A/B/B

B/B/B/A  B/B/A/B  A/A/B/B  A/B/A/B  A/B/B/A  B/B/A/A

B/A/B/A  B/A/A/B  A/A/A/B  B/A/A/A  A/B/A/A  A/A/B/A
```

Administration of the peptides of the present invention to a patient will follow general protocols for the administration of antibiotics, taking into account the toxicity, if any. It is expected that the treatment cycles would be repeated as necessary. Listed below are some common antibiotics and their respective dosages.

D. Liposomal Delivery

In particular embodiments, the peptides of the present invention may be used in conjunction with lipid delivery vehicles, often called liposomes. A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures and entrap water and dissolved solutes between the lipid bilayers (Ghosh and Bachhawat, 1991). Lipophilic molecules or molecules with lipophilic regions may also dissolve in or associate with the lipid bilayer.

A liposome used according to the present invention can be made by different methods, as would be known to one of ordinary skill in the art. For example, a phospholipid (Avanti Polar Lipids, Alabaster, Ala.), such as for example the neutral phospholipid dioleoylphosphatidylcholine (DOPC), is dissolved in tert-butanol. The lipid(s) is then mixed with the imexon and/or a derivative thereof, and/or other component (s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at −20° C. and can be used up to three months. When required the lyophilized liposomes are reconstituted in 0.9% saline. The average diameter of the particles obtained using Tween 20 is about 0.7 to about 1.0 µm in diameter.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In other alternative methods, liposomes can be prepared in accordance with other known laboratory procedures (e.g., see Bangham et al., 1965; Gregoriadis, 1979; Deamer and Nichols, 1983; Szoka and Papahadjopoulos, 1978, each incorporated herein by reference in relevant part). These methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

The size of a liposome varies depending on the method of synthesis. Liposomes in the present invention can be a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040; U.K. Patent Application GB 2193095 A; Mayer et al., 1986; Mayhew et al., 1984, each incorporated herein by reference).

A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

The production of lipid formulations often is accomplished by sonication or serial extrusion of liposomal mixtures after (I) reverse phase evaporation (II) dehydration-rehydration (III) detergent dialysis and (IV) thin film hydration. In one aspect, a contemplated method for preparing liposomes in certain embodiments is heating sonicating, and sequential extrusion of the lipids through filters or membranes of decreasing pore size, thereby resulting in the formation of small, stable liposome structures. This preparation produces liposomes only of appropriate and uniform size, which are structurally stable and produce maximal activity. Such techniques are well-known to those of skill in the art (see, for example Martin, 1990).

Numerous disease treatments are using lipid based gene transfer strategies to enhance conventional or establish novel therapies. Advances in liposome formulations have improved the efficiency of gene transfer in vivo (Templeton et al., 1997) and it is contemplated that liposomes are prepared by these methods. Alternate methods of preparing lipid-based formulations for nucleic acid delivery are described (WO 99/18933).

In another liposome formulation, an amphipathic vehicle called a solvent dilution microcarrier (SDMC) enables integration of particular molecules into the bilayer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

E. Therapeutic Uses

1. Formulations and Routes of Administration

Pharmaceutical aqueous compositions of the present invention comprise an effective amount of a peptide dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The compositions will be sterile, be fluid to the extent that easy syringability exists, stable under the conditions of manufacture and storage.

The actual dosage amount of a composition of the present invention administered to a patient can be determined by physical and physiological factors such as body weight, severity of condition, idiopathy of the patient and on the route of administration. With these considerations in mind, the dosage of a lipid composition for a particular subject and/or course of treatment can readily be determined.

Although it is most preferred that compositions of the present invention be prepared in sterile water containing other non-active ingredients, made suitable for injection, solutions of such active ingredients can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

2. Indications

ErbB-2 is overexpressed in a number of cancer types including those involving the female genital tract (e.g., endometrial cancer), gastric cancer and prostate cancer. A preliminary clinical study using a variant of Herceptin™ showed some improvement in patients with prostate and kidney cancer. However, a primary target for ErbB-2 targeted therapies is breast cancer, of which 20-30% show overexpression of this marker. Thus, in accordance with the present invention, there are provided therapeutic methods designed to intervene in such ErbB-2 related cancers. These therapies may facilitate tumor growth inhibition, reduction in tumor size, induction of apoptosis in tumor cells, inhibition or reduction in metastasis formation, or otherwise result in an improvement in the clinical situation of a cancer patient, including improving one or more symptoms of cancer.

The compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally using aerosol, injection, infusion, continuous infusion, localized perfusion bathing target cells directly or via a catheter or lavage. In particular, the invention may provide local, regional or systemic administration with respect to the tumor location. Typically, such compositions are prepared as injectables, either as liquid solutions or suspensions; solid forms suitable for preparing solutions or suspensions upon the addition of a liquid prior to injection can also be prepared; and the preparations can also be emulsified.

F. Kits

Any of the compositions described herein may be comprised in a kit. In a non-limiting example, a peptide or analogue thereof may be comprised in a kit. The kits will thus comprise, in suitable container means, a peptide, with optional additional agents of the present invention, such as linking reagents or diagnostic or therapeutic agents.

The kits may comprise a suitably aliquoted peptide or analogues thereof, whether conjugated or not. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such means may include injection or blow-molded plastic containers into which the desired vials are retained.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture and Maintenance. The HEK-293 human embryonic kidney cells, as well as DU-145 human prostate carcinoma, and T-24 human bladder carcinoma cell lines were purchased from ATCC. The MDA-MB-435 human breast carcinoma cell line was kindly provided by Dr. Janet E. Price, M. D. Anderson Cancer Center, Houston, Tex. All cells were maintained as monolayer cultures in either DMEM (HEK-293 human embryonic kidney cells) or RPMI-1640 (DU-145 human prostate carcinoma, MDA-MB435 human breast carcinoma, and T-24 human bladder carcinoma cells) medium supplemented with 10% fetal bovine serum (FBS), sodium pyruvate, nonessential amino acids, and L-glutamine. The cultures were maintained at 37° C. in a 5% $CO_2$ humidified incubator. Subculturing was performed using standard trypsinization procedures.

Expression and Purification of ErbB-2-ECD. The eukaryotic expression plasmid c-erbB-2-pRc/$CMV_{FLAG}$ encoding ErbB-2-ECD tagged with a FLAG epitope at C-terminus was used to create a cell line stable expressing the FLAG-tagged ErbB2-ECD fusion protein (Clark et al., 1997). The human embryonic kidney cells HEK-293 were transfected with 20 µg of recombinant DNA using a calcium phosphate precipitation kit (Stratagene) in accordance to manufacturer's protocol. Stable transfectants were selected in medium (DMEM+10% FBS) containing G418 (0.5 mg/ml). Individual clones arising from single cells were isolated using 8×10 cloning cylinders (Sigma). The supernatant from each clone was assayed for the expression of recombinant protein by Western blot and ELISA using Neu (9G6) anti-ErbB-2 mouse monoclonal antibody (Santa Cruz Biotechnology). The highest expressing clone was chosen for future studies.

The filtered supernatant taken from HEK293 cells that secreted ErbB-2-ECD into the medium, was run on anti-FLAG M2 affinity column equilibrated with 20 mM Tris (pH=8.0), 150 mM NaCl. Bound protein was eluted with 0.1 M glycine (pH=3.0) and neutralized with 1M Tris HCl (pH=8.0). The protein was concentrated and dialyzed against PBS, and $NaN_3$ was added to prevent bacterial growth.

Western Blot Analysis of ErbB-2-ECD. Purified ErbB-2-ECD was subjected to SDS-polyacrylamide gel electrophoresis (Laemmli, 1970), and transferred to a nitrocellulose filter. The filter was subsequently blocked with 1% BSA in PBS (pH=7.4), and exposed to Neu (9G6) anti-ErbB-2 mouse monoclonal antibody. The bound antibody was detected by anti-mouse secondary antibody coupled to alkaline phosphatase. Color reaction was performed using 5-bromo-4-chloro-3indonyl phosphate (BCIP) and nitro blue tetrazolium (NBT).

Size-Exclusion HPLC Analysis. Size-exclusion chromatography was performed on a BIOPSEP SEC-S2000 column equilibrated with 0.05 M phosphate buffer pH=6.8. A flow rate of 0.5 ml/min was maintained throughout the studies. The elution volume of dextran served as void volume. Trypsin inhibitor, chicken egg albumin, human albumin, and mouse IgG served as molecular weight markers. Recombinant ErbB-2-ECD (10 µg) was used to inject the column. The elution volume for each injected protein was measured as a function of protein molecular weight.

Affinity Selection. The affinity selection was performed following a protocol described by Smith and Scott (1993). Briefly, wells of the microtiter plates were first coated with streptavidin, washed with TPBS (phosphate buffered saline, pH 7.4, 0.5% (v/v) Tween-20), and then blocked with 3% (w/v) BSA. Biotinylated antigen was incubated with streptavidin coated plates for 2 hours at 4° C. In first and second round of selection 10 µg of biotinylated antigen per plate was added, in third round amount of antigen was decreased to 1 µg, and for fourth round of selection 0.1 µg of antigen was used. Unoccupied biotin-binding sites were blocked with 0.1 mM biotin. Phage was incubated with antigen for 4 hrs at RT. Plates were washed 10 times with TPBS to remove unbound phage. Bound phage was eluted with elution buffer (0.1 M HCl, pH is adjusted to 2.2 with glycine, 1 mg/ml BSA, 0.1 mg/ml phenol red) at RT during 10 min. The increased percentage of bound phage to input phage (yield) was an intrinsic characteristic of successful biopanning. After each round, except the last, the eluate of the bound phage was propagated and used as input for the next round. Individual clones were characterized by DNA sequencing after the fourth round of selection.

DNA sequencing analysis. Individual phage isolates were sequenced manually by a modified dideoxy sequencing methodology as described by Haas and Smith (1993).

Sequence Comparison. The sequence homology searches were performed using the FASTA program of the University of Wisconsin Genetics Computer Group program package (GCG, version 10.0-Unix, January 1999). EMBL and PIR-protein databases were released March 1997 and June 1999 respectively.

Peptide Synthesis. The peptides were chemically synthesized on the Applied Biosystems peptide synthesizer 431A using FMOC-based chemistry.

Mass spectrometric analysis. Mass Consortium Corporation, San Diego, performed the mass spectrometric analysis. Commercially available oxidized form of gluthatione (Sigma # G4501) was used as control for reduction conditions.

Immunoblot analysis of binding activity of the p6.1 peptide. ErbB-2-ECD and three other proteins, bovine serum albumin (BSA, Sigma #A-3912), asialofetuin (AF, Sigma #A-4781), and human IgG (Sigma #I-2511) were immobilized on a nitrocellulose membrane at various quantities (6.25-50 ng) and then incubated with 1% blocking reagent (Boehringer Mannheim, cat # 1096 176) in phosphate buffered saline (PBS) pH=7.4. After washing three times with PBS, the membrane was incubated with 100 µM biotinylated peptide for 2 hrs at RT. The membrane was washed and incubated with alkaline phosphatase labeled streptavidin (Sigma #S-2890) for 1 hr RT. The staining reaction was performed using 50 µl NBT and 37.5 µl X-phosphate solutions (Boehringer Mannheim, cat # 1383 213) in 10 ml 0.1M Tris buffer, pH=9.5, 0.05 MMgCl, 0.1 M NaCl.

ELISA. 100 ng of ErbB-2-ECD or ErbB1 (Sigma # E-2645) in PBS was applied to polystyrene wells (Costar #3590) overnight at +4° C. Coated wells were washed three times with TPBS (phosphate buffered saline, pH 7.4, 0.5% (v/v) Tween-20) and blocked with 1% blocking reagent (Boehringer Mannheim # 1096 176) in PBS for 1 hr at RT. Wells were subsequently incubated with biotinylated peptide added to the wells by serial dilutions (1:2) at RT for 2 hr. After washing three times with TPBS, wells were incubated with alkaline phosphatase labeled streptavidin (Sigma # S-2890) for 1 hr at RT. Bound alkaline phosphatase was developed using 1 mg/ml p-Nitrophenyl Disodium Phosphate (Sigma # N-9389) in 1M diethanolamine buffer, 0.5 mM $MgCl_2$, pH=9.8. The pNPP reaction was stopped with 3M NaOH. Optical density was measured at 405 nm in a microplate reader. All assays were performed at least three times in triplicate wells. Values are reported as an average of absorbence +/−SD.

Cell Binding Assay. DU-145 human prostate adenocarcinoma), MDA-MB-435 (human breast carcinoma), and T-24 (human bladder carcinoma) cells were grown directly on the same microscope slide using a 4 well Lab-Tek II chamber slide system (Nalge Nunc). When cultures reached approximately 60-70% confluence, the cells were briefly washed with PBS, fixed with 4% formaldehyde solution in PBS for 30 min but not permeabilized, and preblocked for 1 hr with 2% bovine serum albumin (BSA) solution in PBS at 37° C. The cultivation chambers were removed and cells were incubated for 2 hr with solution of Neu (9G6) anti-ErbB-2 mouse monoclonal antibody (Santa Cruz Biotechnology) diluted 1:100 and biotinylated peptide (100 µM) in 2% solution BSA in PBS. The slides were washed three times with PBS followed by 1 hr incubation with Lissamine Rhodamineconjugated donkey anti-mouse IgG (Jackson ImmunoResearch Laboratories) and streptavidin-AMCA-S conjugate (Molecular Probes) in 2% BSA in PBS. After additional washes with PBS, the slides were mounted and analyzed by fluorescent microscopy using Rhodamine and UVA filter sets.

Fluorescence assay. The fluorescence titration studies were carved out using a SLM Aminco spectrofluorometer interfaced to a DEL 433/L PC running SLM Aminco 8100 series 2 software. The titrations were performed at 25° C. with varying amounts of peptide added to a fixed ErbB-2-ECD concentration (200-600 nM) in 2 ml of phosphate buffered saline (pH=7.4). Each measurement was collected for 5-20 sec after 1-2 min pre-equilibration. The excitation shutter remained closed during pre-equilibration of the sample and was opened only during data acquisition in order to minimize photobleaching of the sample. The fluorescence measurements were corrected for dilutions and photobleaching of ErbB-2-ECD. Values reported are an average of three independent measurements. The difference between total peptide concentration and free peptide concentration was neglected since the concentration of the peptide was much higher than concentration of the protein during the entire experiment. The fitting procedure was performed using Origin (Microcal Software Inc).

Example 2

Results

Purification and characterization of the recombinant extracellular domain of ErbB-2. The ECD of human ErbB-2 tagged with the FLAG epitope DYKDDDDK (SEQ ID NO:2) was expressed in human embryonic kidney cells (HEK-293) and purified by anti-FLAG affinity chromatography (Clark et al., 1997). The identity of the recombinant protein was confirmed by Western blot analysis with Neu (9G6) anti-ErbB-2 mouse monoclonal antibody. The purified protein yielded a single species by SDS-PAGE analysis with molecular weight of approximately 90 kDa. However, size exclusion HPLC analysis under non-denaturing conditions revealed the molecular weight of the recombinant ECD two fold higher than SDS-PAGE electrophoresis ~182 kDa, suggesting the existence of the protein as a homodimer in solution. This is consistent with previously reported observations describing the ErbB-2-ECD in sera from patients with various carcinomas as a homodimer with MW ~200 kDa (Wu et al., 1993). The affinity purified ErbB-2ECD was biotinylated and used in the biopanning procedures.

Isolation of peptide sequences that bind ErbB-2 extracellular domain. A random 6-amino acid peptide bacteriophage display library was affinity selected against the ErbB-2-ECD to identify novel peptide-ligands. The library was based on the fUSE5 bacteriophage vector encoding the foreign peptide insert in N-terminus of minor coat protein pIII (Scott and Smith, 1990). Four rounds of affinity selection were employed to enrich phage populations for virions that displayed peptides with affinity to ErbB-2-ECD (Table 1). The analysis of 100 clones from the affinity selected phage population revealed three groups of clones. The largest group, which accounted for 75% of the sequenced clones, contained an insert encoding the KCCYSL peptide (p6.1). Within this group several nucleotide sequences were found with different bases in the third position of codons but the same amino acid sequence. This supports the fact that the peptide was selected due to peptide-protein interaction and not to propagation properties of the particular clone. The remaining clones fell into two groups with similar sequences WYAWML (SEQ ID NO:3)(p6.2) and WYSWLL (SEQ ID NO:4)(p6.3). Futher investigation of the p6.2 and p6.3 peptides were not pursued due to their low presentation in selected phage population and high hydrophobicity.

TABLE 1

Affinity Selected Peptide Sequences

| Name | Peptide Sequence | Library | % Of Clones* |
|---|---|---|---|
| p6.1 | KCCYSL | F3-6 | 75 |
| p6.2 | WYAWML | F3-6 | 8 |
| p6.3 | WYSWLL | F3-6 | 10 |

*The percent of individual clones that were represented in the affinity selected and sequenced phage clones.

Homology analysis of selected p6.1 peptide with known protein sequences. The p6.1 peptide was analyzed for stretches of homology with known protein sequences from PIR (George et al., 1996) and SPTREMBL (Stoesser et al., 1999) protein sequence databases. The results of the FASTA sequence analysis (Pearson et al., 1988) for p6.1 are summarized in Table 2. The six-amino acid p6.1 peptide is found to share a limited linear sequence homology with several different proteins (Table 2), including monocyte chemotactic protein (MCP), whey acidic protein (WAP), human spasmolytic protein (hSP), and the envelope protein of the Rous associated virus 1 (RAV 1 Env). These proteins, each contained five-amino acid stretches of homology to p6.1 with 1 conservative substitution (CCYTL (SEQ ID NO:5), KCCFS (SEQ ID NO:6), KCCFS and CCFSL (SEQ ID NO:7) respectively). Of particular interest was the homology of p6.1 with hSP and RAV 1 Env, since those proteins could be involved in direct interaction with ErbB receptors. Human SP belongs to the trefoil polypeptide family and has been implicated in the transient phosphorylation of ErbB-1 (Taupin et al., 1999). The homology of p6.1 peptide with RAV 1 Env may be indicative of functional significance, since ErbB-1 has been suggested as a possible receptor for several different viruses (Strong and Lee, 1996; Tang et al, 1993).

TABLE 2

Homology of p6.1 peptide with known protein sequences

| Name | Sequence | Position |
|---|---|---|
| p6.1 | KCCYSL | |
| Monocyte Chemotactic Protein, Bovine | CCYTL | 9-13** |
| Whey Acidic Protein, Camel | KCCFS | 97-101** |
| Spasmolytic Protein, Human | KCCFS | 106-110** |
| Envelope Protein, Rous Associated Virus 1 | CCFSL | 9-13* |

$^a$Bold invariant amino acids; regular, equivalent amino acids.
*Amino acid numbers derived from the sequences deposited in STREMBL data bank.
**Amino acid numbers derived from the sequences deposited in PIR data bank.

No linear sequence homology to p6.1 was found in any of the ErbB family ligands. However, the oxidized form of p6.1 could mimic a CC(Y/F) motif formed within the EGF-like domain of all known ErbB ligands due to $C_{14}$-$C_{31}$ (EGF numbering) disulfide bond. Moreover, three of ErbB ligands, amphiregulin (AR), heregulin-(x (HRG-cc), and heregulin-β1 (HRG-(β1), exhibit four-residue homology (KCCF) due to the presence of lysine residue next to the cysteine corresponding to $C_{31}$, of the EGF.

Figure 1B:
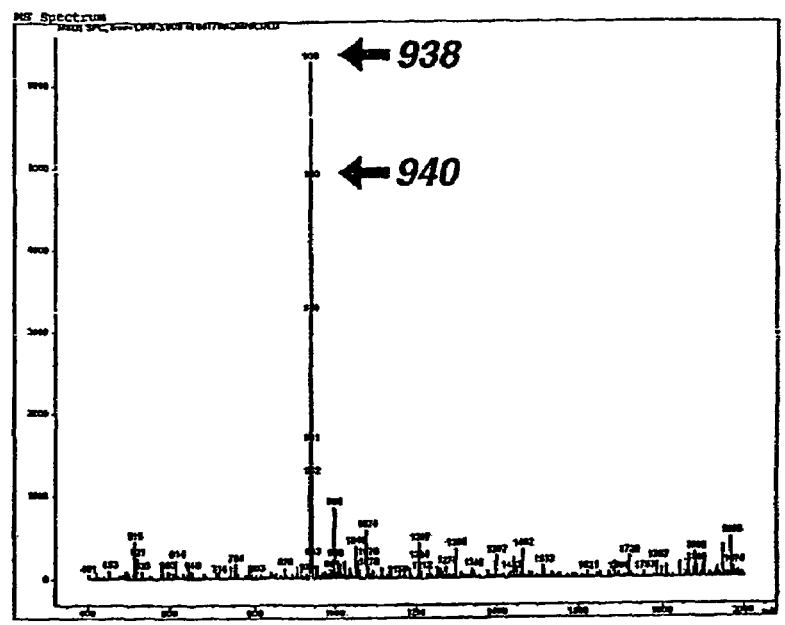

Peptide synthesis and characterization. The p6.1 peptide and its biotinylated analog were chemically synthesized and purified to examine their binding activity in the absence of phage particle. Electrospray mass spectrometry was employed to confirm the molecular weight of the peptides and examine their conformations. Since the p6.1 sequence contained two cysteine residues, the peptide could exist in a reduced form, as an oxidized monomer, as a disulfide-bridged dimer or as a mixture. FIG. 1A shows electrospray ionization mass spectrum (ESI-MS) of p6.1. The major peak corresponds to the ion [M*–H]$^-$ at m/z 712 where M* is molecular weight of oxidized form of a single p6.1 molecule. There is also a peak at m/z 714, which is attributed to the reduced form of p6.1 [M–H]$^-$. FIG. 1B shows ESI-MS of biotinylated p6.1. There are two major peaks from the reduced p6.1 monomer ion [M*–H]$^-$ at m/z 940 and from the oxidized p6.1 monomer [M–H]$^-$ at m/z 938. These results suggest that the peptide exists in solution in two forms as an oxidized monomer and a reduced monomer. The mass spectrum method did not detect any presence of dimerized peptide in solution, which was consistent with the HPLC analysis. Since the molecules become protonated during the ionization procedure, reduction conditions of the ESI technique on disulfide bond stability were analyzed. For this purpose a commercially available oxidized glutathione, that exists as a disulfide-bonded peptide dimer (MW=612) was used. Mass spectrum of glutathione contained two major peaks from the ion [M–H]$^-$ at m/z 611 and from the [M–2H]$^{2-}$ at m/z 305. There was no peak that corresponded to the reduced form of glutathione. Thus, the ESI procedure did not appear to reduce disulfide bridges and could be used for detection of the oxidized forms of the peptide.

Binding activity of p6.1 peptide. The binding specificity of synthetic p6.1 peptide to recombinant ErbB-2-ECD was examined by immunoblot and ELISA procedures. Immunoblot analysis was performed to compare the binding activity of the p6.1 peptide to ErbB-2-ECD and several other non-ErbB-2 related proteins. Purified recombinant ErbB-2-ECD as well as BSA, bovine asialofetuin, and human IgG were spotted on a nitrocellulose membrane at various amounts and exposed to the biotinylated p6.1 peptide. The p6.1 peptide bound only ErbB-2 and did not react with control proteins (FIG. 2A). Further ELISA analysis was performed to compare: first, binding activities of p6.1 and control peptide to ErbB-2ECD and second, the binding activity of p6.1 to ErbB-2-ECD and to ErbB-1 receptor, which is a member of the same RTK family. Recombinant ErbB-2-ECD and ErbB1 receptor from human carcinoma A431 cells were applied to plastic dishes and then incubated with the various concentrations of biotinylated p6.1 and a control peptide (biotin-RRLLFYKYVYKRYRAGKQRG (SEQ ID NO:8)). The p6.1 peptide demonstrated significant dose dependent binding activity to both ErbB-2-ECD and ErbB-1 protein, while the control peptide did not bind either ErbB-2-ECD or ErbB-1 (FIG. 2B).

Fluorescence quenching studies were performed in order to evaluate the equilibrium dissociation constant of p6.1 to the soluble Erb-2-ECD. Intrinsic tryptophan fluorescence of the protein was monitored as a function of peptide concentration. Since p6.1 peptide contains a tyrosine residue, samples were excited at 300 nm and monitored at 350 nm to minimize the influence of tyrosine emission on tryptophan fluorescence. Titration of ErbB-2-ECD with p6.1 resulted in substantial decrease of tryptophanyl fluorescence with maximum quenching of 20% under saturation conditions. In the analysis, the inventors assumed a model with the stoichiometric ratio of protein to peptide equal to 1:1. The data were collected at 2μM, 4 μM and 6 μM concentrations of the protein. Theoretical curves were generated for the percentage of fluorescence quenching as a function of total peptide concentration (FIG. 2C). An apparent equilibrium dissociation constant, $K_d$=30.2×/–7.6 μM, was determined using a nonlinear least-squares curve fitting procedure, which was applied to all three sets of data points obtained at different concentrations of protein with $K_d$ as the shared constant for all curves.

Direct Cell Binding Assay. The ability of the p6.1 to recognize cultured human cancer cells expressing native conformation of the ErbB-2 was examined. High levels of ErbB-2 expression on DU-145 human prostate carcinoma cells has been reported previously (Zhau et al., 1992). The MDA-MB-435 human breast carcinoma cells were shown to express moderate levels of the ErbB-2 protein (Hynes and Stem, 1994). In double immunostaining studies both the anti-ErbB-2 mouse monoclonal antibody, and biotinylated p6.1 peptide bound prostate carcinoma cells DU-145 and MDA-MB-435 cells. This result was consistent with experimental ELISA data suggesting that the Neu (9G6) antibody used in the studies and the p6.1 peptide do not compete for the same binding site on the extracellular domain of oncoprotein. The biotinylated control peptide (biotin-RRLL-FYKYVYKRYRAGKQRG) did not bind DU-145 or MDA-MB-435 cells. Neither the Neu (9G6) anti-ErbB-2 antibody, nor the biotinylated p6.1 bound T-24 human bladder carcinoma cells used as negative control.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

H. REFERENCES

The following references, to the extent that they provide exemplary procedural or other details supplementary to those set forth herein, are specifically incorporated herein by reference.

U.S. Pat. No. 4,162,282
U.S. Pat. No. 4,310,505
U.S. Pat. No. 4,472,509
U.S. Pat. No. 4,533,254
U.S. Pat. No. 4,728,575
U.S. Pat. No. 4,728,578
U.S. Pat. No. 4,737,323
U.S. Pat. No. 4,921,706
U.S. Pat. No. 4,938,948
U.S. Pat. No. 5,021,236
U.S. Pat. No. 5,401,511
U.S. Pat. No. 5,440,013
U.S. Pat. No. 5,446,128
U.S. Pat. No. 5,475,085
U.S. Pat. No. 5,603,872
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,879,703
U.S. Pat. No. 5,889,155
U.S. Pat. No. 5,929,237
Alimandi et al., *EMBO J*, 16(18):5608-17, 1997.
Arap et al., *Cancer Res.*, 55(6):1351-1354, 1995.
Bakhshi et al., *Cell*, 41(3):899-906, 1985.
Ballinger et al., *J. Biol. Chem.*, 273(19):11675-11684, 1998.
Bangham et al., *J. Mol. Biol.*, 13:238, 1965.
Baselga et al., *Cancer Res.*, 58:2825-2831, 1998.
Bodanszky et al., *J. Antibiot*, 29(5):549-53, 1976.
Burbage et al., *Leuk Res*, 21(7):681-690, 1997.
Caldas et al., *Nat. Genet.*, 8(1):27-32, 1994.
Cheng et al., *Cancer Res.*, 54(21):5547-5551, 1994.
Clark et al., *Clin. Exp. Inmunol.*, 109:166-174, 1997.
Cleary and Sklar, *Proc. Natl. Acad. Sci. USA*, (21):7439-7443, 1985.
Cleary et al., *J. Exp. Med.*, 164(1):315-320, 1986.
Culver et al., *Science*, 256(5063):1550-1552, 1992.
De Potter et al., *Histopathol.*, 15:351-362, 1989.
Deamer and Nichols, Proc Natl Acad Sci USA, 80(1):165-8, 1983.
Devlin et al., *Science*, 249:404-406, 1990.
Disis et al., *Clin. Cancer Res.*, 5(6):1289-1297, 1999.
Doorbar and Winter, J. Mol. Biol., 244(4):361-369, 1994.
Downward et al., *Nature*, 307(5951):521-7, 1984.
Fischman et al., *J. Nucl. Med.*, 34(12):2253-2263, 1993.
George et al., *Nucl. Acids Res.*, 24:17-20, 1996.
Ghosh and Bachhawat, In: *Liver Diseases, Targeted Diagnosis and Therapy Using Specific Receptors and Ligands*. Wu et al., eds., Marcel Dekker, New York, pp. 87-104, 1991.
Giebel et al., *Biociemistry*, 34:15430-15435, 1995.
Gregoriadis, In: *Drug carriers in biology and medicine*, G. Gregoriadis (ed.), 1979.
Haas and Smith, *Biotechniques*, 15:422-424, 1993.
Harris et al., *Gene Ther.*, 1(3):170-175, 1994.
Hollstein et al., *Science*, 253(5015):49-53, 1991.
Hussussian et al., *Nat. Genet.*, 8(1):15-21, 1994.
Hynes and Stem, *Biochim. Biophys. Acta*, 1198:165-184, 1994.
Jinno et al., *Surg. Today*, 26(7):501-507, 1996.
Johnson et al., In: *Biotechnology And Pharmacy*, Pezzuto et al., eds., Chapman and Hall, New York, 1993.
Jones et al., *J. Biol. Chem.*, 273(19):11667-11674, 1998.
Kamb et al., *Nat. Genet.*, 8(1):23-2, 1994.
Kay et al., *Gene*, 128:59-65, 1993.
Kerr et al., *Br. J. Cancer*, 26(4):239-257, 1972.
Klaassen, In: *The Pharmacological Basis of Therapeutics*, Goodman and Gilman, Eds., Pergamon Press, 8th Ed., pp. 49-61, 1990.
Laemmli, *Nature*, 227:680, 1970.
Lidor et al., *Am. J. Obstet. Gynecol.*, 177(3):579-585, 1997.
Martin, *J Biol Chem*, 265(34):20946-20951, 1990.
Massuda et al., *Proc. Natl. Acad. Sci. USA*, 94(26):14701-14706, 1997.
Mayer, *Biochim Biophys Acta*, 858(1):161-8, 1986.
Mayhew et al., *Biochim Biophys Acta*, 775(2):169-74, 1984.
McInnes and Sykes, *Biopolymers*, 43(5): 339-366, 1997.
McOmie, Protective Groups in Organic Chemistry, Plenum Press, New York, N.Y., 1973.
Merrifield, *Science*, 232(4748):341-347, 1986.
Murayama et al., *J. Biochem.* (Tokyo), 120(2):445-451, 1996.
Nobori et al., *Nature*, 368(6473):753-756, 1994.
Okamoto et al., *Proc Natl Acad Sci USA*, 1(23):11045-11049, 1994.
Oldenburg et al., *Proc. Nat'l Acad. Sci. USA*, 89:5393-5397, 1992.
Orlow et al., *Int. J. Oncol.*, 15(1):17-24, 1994.
PCT/US85/01161
PCT/US89/05040
Pearson and Lipman, *Proc. Nat'l Acad. Sci. USA*, 85(8):2444-2448, 1988.
Peletskaya et al., *J. Mol. Biol.*, 270:374-384, 1997.
Peletskaya et al., *Mol. Diversity*, 2:13-18, 1996.
Peptide Synthesis, John Wiley & Sons, 2d Ed.; Kent & Clark-Lewis In: Synthetic Peptides in Biology and Medicine, Alitalo et al. (Eds.), 295-358, Science Publishers, (Amsterdam, 1985)
Piccart et al., In: *American Society of Clinical Oncology Educational Book*, Perry (Ed), American Soc. Clinical Oncology, Alexandria, Va., 1999.
Ravindranath and Morton, *Intern. Rev. Immunol.*, 7: 303-329, 1991.

Remington's Pharmaceutical Sciences, 15th ed., pages 1035-1038 and 1570-1580, Mack Publishing Company, Easton, Pa., 1980.
Renschler et al., *Cancer Res.*, 55(23):5642-5647, 1995.
Rosenberg et al., *Ann. Surg.* 210(4):474-548, 1989.
Rosenberg et al., *N. Engl. J.Med.*, 319:1676, 1988.
Schechter et al., *Nature,* 312(5994):513-516, 1984.
Scott and Smith, *Science,* 249:386-390, 1990.
Serrano et al., *Nature,* 366:704-707, 1993.
Serrano et al., *Science,* 267(5195):249-252, 1995.
Shelly et al., *J. Biol. Chem.*, 273(17):10496-10505, 1998.
Shih et al., *Nature,* 290(5803):261-4, 1981.
Slamon et al., *Science,* 235(4785):177-82, 1987
Smith and Rutledge, *Natl. Cancer Inst. Monogr.*, 42:141-143, 1975.
Smith and Scott, *Methods Enzymol.* 217:228-257, 1993.
Stoesser et al., *Nucl. Acids Res.*, 27(1):18-24, 1999.
Strong and Lee, *J. Virol.*, 70:612-616, 1996.
Stuart and Young, Solid Phase Peptide Synthelia, Pierce Chemical Company, Rockford, Ill., 1984.
Szoka and Papahadjopoulos, *Proc. Nat'l Acad. Sci. USA,* 75:4194-4198, 1978.
Taupin et al., *J. Clin. Invest.*, 103:R31-R38, 1999.
Templeton et al., *Nat Biotechnol.* 15(7):647-652, 1997.
Tsujimoto and Croce, *Proc Natl Acad Sci USA*. 83(14):5214-5218, 1986.
Tsujimoto et al., *Science,* 228(4706):1440-1443, 1985.
U.K. Pat App. GB 2193095 A
WO 99/18933
Weinberg, *Science,* 254(5035):1138-1146, 1991.
Weiner et al., *Cancer Res.*, 55(20):4586-4593, 1995.
Wienchen and Dietel, Int. J. Cancer, 63(4):604-608, 1995.
Wrighton et al., *Science,* 273:458-463, 1996.
Wu et al., *J. Clin. Lab. Anal.*, 7:31-40, 1993.
Young et al., *N Engl J Med.* 7:299(23):1261-1266, 1978.
Zhau et al., *Mol. Carcinogenesis,* 5(4):320-327, 1992.

The invention claimed is:

1. A method for targeting an agent to a cancer cell expressing ErbB-2 comprising bringing said cancer cell into contact with a peptide-agent complex, wherein said peptide comprises the sequence KCCYSL (SEQ ID NO:1) and said peptide binds to the extracellular domain of ErbB-2, wherein said agent is a diagnostic agent, a chemotherapeutic, a radiotherapeutic, a toxin or a cytokine.

2. The method of claim 1, wherein said agent is a diagnostic agent.

3. The method of claim 2, wherein said diagnostic agent is a radiolabel, a chemilluminescent label, a fluorescent label, a magnetic spin resonance label, or a dye.

4. The method of claim 3, wherein the diagnostic agent is a radiolabel selected from the group consisting of astatine$^{211}$, $^{51}$chromium, $^{36}$chlorine, $^{57}$cobalt, $^{58}$cobalt, copper$^{67}$, $^{152}$europium, gallium$^{67}$, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, lutetium$^{177}$, samarium$^{153}$, holmium$^{166}$, bisumth$^{212}$, bisumuth$^{213}$ and actinium$^{225}$, 5. The method of claim 1, wherein said agent is a chemotherapeutic agent.

6. The method of claim 1, wherein said agent is a radiotherapeutic agent.

7. The method of claim 1, wherein said peptide is between 6 and about 100 residues in length.

8. The method of claim 7, wherein said peptide is between 6 and about 50 residues in length.

9. The method of claim 8, wherein said peptide is between 6 and about 25 residues in length.

10. The method of claim 9, wherein said peptide is between 6 and about 15 residues in length.

11. The method of claim 1, wherein said cancer cell is a breast cancer cell.

12. The method of claim 1, wherein said cancer cell is a prostate cancer cell.

13. The method of claim 1, wherein said complex further comprises a linking moiety that connects said agent and said peptide.

14. The method of claim 13, wherein said linking moiety is linked to said peptide through the N-terminal amine, the C-terminal carboxyl group, or a side chain.

15. The method of claim 1, wherein said cancer cell is located in a subject.

16. The method of claim 15, wherein is said subject is a human.

17. The method of claim 15, wherein said complex is delivered local or regional to said cell.

18. The method of claim 15, wherein said complex is delivered systemically.

19. The method of claim 1, wherein said complex is delivered into the vasculature of a tumor comprising said cell.

20. The method of claim 1, wherein said agent is a toxin.

21. The method of claim 1, wherein said agent is a cytokine.

* * * * *

UNITED STATES PATENT AND TRADEMARK OFFICE
CERTIFICATE OF CORRECTION

| | |
|---|---|
| PATENT NO. | : 7,585,509 B2 |
| APPLICATION NO. | : 10/520408 |
| DATED | : September 8, 2009 |
| INVENTOR(S) | : Thomas P. Quinn et al. |

It is certified that error appears in the above-identified patent and that said Letters Patent is hereby corrected as shown below:

In title page, item (54) title, delete "ERB-2" and insert -- ErbB-2 -- therefor.

In column 1, line 1, delete "ERB-2" and insert -- ErbB-2 -- therefor.

In claim 4, column 42, line 67, delete the "," and insert a --.--.

Signed and Sealed this

Seventeenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,585,509 B2
APPLICATION NO. : 10/520408
DATED : September 8, 2009
INVENTOR(S) : Quinn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 374 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Lys Cys Cys Tyr Ser Leu
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Asp Tyr Lys Asp Asp Asp Asp Lys
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Trp Tyr Ala Trp Met Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide
```

```
<400> SEQUENCE: 4

Trp Tyr Ser Trp Leu Leu
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Cys Cys Tyr Thr Leu
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Lys Cys Cys Phe Ser
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Cys Cys Phe Ser Leu
 1               5

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Arg Arg Leu Leu Phe Tyr Lys Tyr Val Tyr Lys Arg Tyr Arg Ala Gly
 1               5                  10                  15

Lys Gln Arg Gly
            20
```